(12) United States Patent
Tanaka et al.

(10) Patent No.: US 6,905,671 B1
(45) Date of Patent: Jun. 14, 2005

(54) DIAGNOSTIC AGENTS AND REMEDIES FOR MALIGNANT TUMORS

(75) Inventors: Tohru Tanaka, Saitama (JP); Hiroshi Sasaki, Tokyo (JP)

(73) Assignees: Cosmo Research Institute, Tokyo (JP); Cosmo Oil Co., Ltd., Tokyo (JP)

( * ) Notice: Subject to any disclaimer, the term of this patent is extended or adjusted under 35 U.S.C. 154(b) by 0 days.

(21) Appl. No.: 09/445,963

(22) PCT Filed: Jun. 16, 1998

(86) PCT No.: PCT/JP98/02648

§ 371 (c)(1),
(2), (4) Date: Dec. 16, 1999

(87) PCT Pub. No.: WO98/57668

PCT Pub. Date: Dec. 23, 1998

(30) Foreign Application Priority Data

Jun. 18, 1997 (JP) .......................... P.9-160945

(51) Int. Cl.$^7$ .............................. A61K 51/04
(52) U.S. Cl. .................. 424/9.6; 514/538; 514/551
(58) Field of Search ................. 424/1.37, 9.6; 514/551, 538, 863, 947; 560/155; 436/64, 81

(56) References Cited

FOREIGN PATENT DOCUMENTS

| JP | 02111747 | * | 4/1990 | |
|----|----------|---|--------|---|
| JP | 2-111747 | | 4/1990 | ......... C07C/229/22 |
| JP | 4-9360 | | 1/1992 | ......... C07C/229/29 |
| JP | 5-38294 | | 2/1993 | ........... C12P/17/18 |
| WO | WO 95-07077 A | | 3/1995 | |
| WO | 97-03042 | | 1/1997 | ......... C07C/229/22 |

OTHER PUBLICATIONS

Creighton, T (1993, Proteins, 2nd edition, W. H. Freeman and Company, NY, pp. 238–243 only).*
Definition of "isotopes" Merriam–Webster Online downloaded on Sep. 16, 2004 from url>>www.m–w.com.*
Kennedy et al., 1994, ACS Symp. Ser., pp. 291–302.*
Jichlinski, et al., 1996, Pro. SPIE–Int. Soc. Opt. Eng. pp. 340–347.*
And Jaffe, et al., 1990, Biochemistry, pp. 8345–8350.*
Z.Hua et al., Effectiveness of δ–Aminolevulinic Acid–induced Protoporphyrin as a Photosensitizer for Photodynamic Therapy in Vivo. Cancer Res., vol. 55, No. 8, p. 1723–31, Apr. 15, 1995.
J. Wang et al., An Efficient Synthesis of δ–Aminolevulinic Acid (ALA) and Its Isotopomers, Tetrahedron Letters, vol. 38, No. 5, p. 739–740, 1997.
Internal Search Report.
Gibson S L et al; " Time–dependent intracellular accumulation of delta–aminolevulinic acid, induction of porphyrin synthesis and subsequent phototoxicity." Photochemistry and Photobiology. Mar. 1997, vol. 65, No. 3, Mar. 1997, pp. 416–421, XP008030491.

* cited by examiner

Primary Examiner—Larry R. Helms
Assistant Examiner—Misook Yu
(74) Attorney, Agent, or Firm—Sughrue Mion, PLLC

(57) ABSTRACT

An agent for diagnosing or photokinetically treating malignant tumors, comprising as an active ingredient a compound in which at least one carbon atom of 5-aminolevulinic acid is a carbon isotope and/or a nitrogen atom in its amino group is a nitrogen isotope, or an ester, amide, salt, hydrate or solvate of the compound.

29 Claims, 1 Drawing Sheet

$^1$H-NMR SPECTRUM IN PRODUCTION EXAMPLE 4

DIAGNOSTIC AGENTS AND REMEDIES FOR MALIGNANT TUMORS

This is a 371 of Application No. PCT/JP98/02648 filed Jun. 16, 1988.

TECHNICAL FIELD

The present invention relates to an agent for diagnosing malignant tumors and an agent for photokinetically treating malignant tumors, each comprising a compound replaced with an isotope.

BACKGROUND ART

Even in the present day when a large number of infectious diseases are conquered, malignant tumors are one of the most serious diseases with which human beings are now confronted. Although treatment methods for malignant tumors have been proposed one after another and the therapeutic ratio has been increased, early stage diagnosis of malignant tumors is the most important factor in treating malignant tumors. Accordingly, various types of tumor markers have been proposed for diagnosing malignant tumors at an early stage and various diagnostic agents have already been on the market, but they have problems still remained unsolved in terms of their efficacy. Although a higher value of a tumor marker indicates higher possibility of a malignant tumor, no information can be obtained on the site where the malignant tumor is present.

It has been found recently that hematoporphyrin and derivatives thereof (so called porphyrins) accumulate in malignant tumors specifically, and methods for diagnosing malignant tumors have been developed using the property of these compounds to generate fluorescence by light irradiation. It is known that photophrin® as a typical compound of porphyrins generates an active oxygen by light irradiation to destroy malignant tumors, so that it has been approved as a therapeutic drug for malignant tumors, and a therapeutic method using this compound has been drawing attention as a photokinetically therapy (*Life Science of Porphyrin and Heme*, edited by Porphyrin Research Society, Tokyo Kagaku Dojin (1995)).

It was found in 1994 that protoporphyrin IX which is induced by administration of 5-aminolevulinic acid accumulates in tumors and shows similar effects to porphyrins, and this compound has been drawing attention due to its low toxicity and phototoxicity and quick metabolism in the body in comparison with those of the above-described porphyrins. It is disclosed that by applying this effect, 5-aminolevulinic acid is used as a contrast medium for MRI (magnetic resonance imaging) by replacing a portion of its hydrogen atoms with deuterium (D) (WO 97/03042).

However, the sensitivity of MRI using this contrast medium is not always satisfactory.

In consequence, an object of the present invention is to provide a diagnostic agent which accumulates properly in malignant tumors and can specify the site of tumor with high sensitivity using nuclear magnetic resonance and an agent for photokinetically treating malignant tumors.

DISCLOSURE OF THE INVENTION

In view of the above, the present inventors have conducted intensive studies mainly on the metabolism of 5-aminolevulinic acid and properties of porphyrins, and as a result, found that malignant tumors can be detected with high sensitivity in comparison with the above-described deuterium-replaced compound using a compound obtained by replacing a carbon atom or nitrogen atom of 5-aminolevulinic acid with a corresponding isotope. This isotope-replaced compound has an effect of photokinetically treating malignant tumors equivalent to that of the unreplaced compound. Thus, the present invention has been accomplished.

Accordingly, the present invention provides an agent for diagnosing malignant tumors and an agent for photokinetically treating malignant tumors, each comprising as an active ingredient a compound in which at least one carbon atom of 5-aminolevulinic acid is a carbon isotope and/or a nitrogen atom in its amino group is a nitrogen isotope, or an ester, amide, salt, hydrate or solvate of the compound.

Also, the present invention provides a composition comprising a compound in which at least one carbon atom of 5-aminolevulinic acid is a carbon isotope and/or its amino group nitrogen atom is a nitrogen isotope, or an ester, amide, salt, hydrate or solvate of the compound, and a diagnostically acceptable carrier or a pharmaceutically acceptable carrier.

BEST MODE FOR CARRYING OUT THE INVENTION

Figure 1:
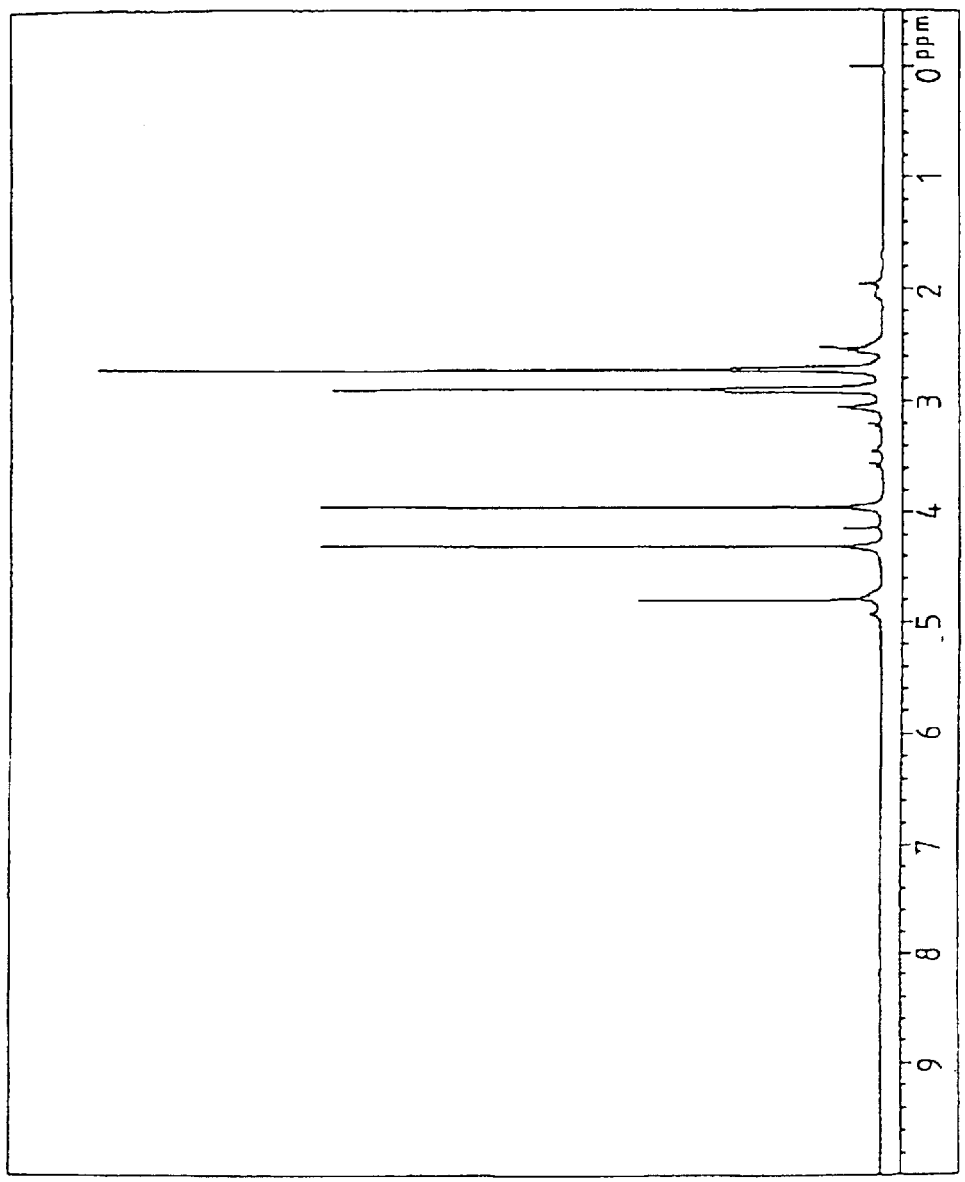
FIG. 1 is a graph showing NMR spectrum of $^{13}$C-replaced 5-aminolevulinic acid obtained in Production Example 4.

When 5-aminolevulinic acid is used as it is, malignant tumors can be detected using nuclear magnetic resonance with high sensitivity in comparison with a case in which this compound is not administered. However, malignant tumors can be detected with higher sensitivity using a compound in which a carbon atom or nitrogen atom of 5-aminolevulinic acid is replaced with a corresponding isotope.

According to the present invention, examples of the carbon isotope include $^{13}$C and $^{14}$C, and $^{13}$C is preferred due to no danger of exposure by radiant rays and superior stability. Also, examples of the nitrogen isotope include $^{13}$N and $^{15}$N, and $^{15}$N is preferred due to the same reasons.

Examples of the compound obtained using $^{13}$C as the carbon isotope include 5-aminolevulinic acid in which at least one of the 2-, 3-, 4- and 5-position carbon atoms is replaced with $^{13}$C.

When this compound is used, malignant tumors can be diagnosed with high sensitivity by measuring $^{13}$C-NMR. Since the naturally existing ratio of $^{13}$C is small, malignant tumors are detected as positive signals. As a matter of course, diagnostic imaging can be easily carried out using a diagnostic imaging apparatus in which the principle of $^{13}$C-NMR is employed.

Also, examples of 5-aminolevulinic acid replaced with a nitrogen isotope include 5-aminolevulinic acid in which a nitrogen atom in its amino group is replaced with $^{15}$N.

When this compound is used, malignant tumors can be diagnosed with high sensitivity by measuring $^{15}$N-NMR. Since the naturally existing ratio of $^{15}$N is small, malignant tumors are detected as positive signals. As a matter of course, diagnostic imaging can be easily carried out using a diagnostic imaging apparatus in which the principle of $^{15}$N-NMR is employed.

In addition, more accurate diagnosis can be carried out by measuring a plurality of NMR using 5-aminolevulinic acid containing both carbon isotope and nitrogen isotope by combining the above-described $^{13}$C-replaced compound and $^{15}$N-replaced compound.

Also, it is possible to carry out diagnosis of malignant tumors by measuring H-NMR using 5-aminolevulinic acid in which at least one of the 2-, 3- and 5-position hydrogen atoms of 5-aminolevulinic acid and hydrogen atoms of the amino group is deuterium ($^2$H or D). However, the ratio of deuterium to be incorporated into protoporphyrin is smaller than the case of carbon atom or nitrogen atom.

Also, a combination with autoradiography is possible when the compound contains radioactive isotopes, such as $^3$H (T) and $^{14}$C, which is markedly useful for research purposes, but it is necessary to take possibility of internal exposure by radiant rays into consideration when used in the human body. In addition, the same application is possible to an oxygen isotope on the carboxylic acid of 5-aminolevulinic acid, but the remaining frequency of oxygen atoms of the carboxylic acid of 5-aminolevulinic acid in protoporphyrin IX is 25% which is smaller than the case of other atoms.

As a reference, the remaining frequency of respective atoms of 5-aminolevulinic acid in protoporphyrin IX and the atomic ratio of protoporphyrin induced from 5-aminolevulinic acid are shown in Table 1.

TABLE 1

| Structure | Remaining frequency | | | Atomic ratio | | |
|---|---|---|---|---|---|---|
| | C | N | H | C | N | H |
| $^1$COOH | 1/4 | — | 0* | 2/34 | — | 0* |
| $\mid$ | 1 | — | 1 | 8/34 | — | 4/32 |
| $^2$CH$_2$ | 1 | — | 3/8 | 8/34 | — | 364 |
| $\mid$ | 1 | — | — | 8/34 | — | — |
| $^3$CH$_2$ | 1 | — | 1/2 | 8/34 | — | 2/32 |
| $\mid$ | — | 1/2 | 1/4 | — | 1 | 1/32 |
| $^4$C═O | | | | | | |
| $\mid$ | | | | | | |
| $^5$CH$_2$ | | | | | | |
| $\mid$ | | | | | | |
| NH$_2$ | | | | | | |

*Substantially 0 due to exchange reaction.

In Table 1, a higher remaining frequency means higher utilization efficiency, and a higher atomic ratio means higher sensitivity. The atomic ratio of a compound in which a plurality of isotopes are replaced is calculated by addition. Each value in the table is per one atom.

As is apparent from Table 1, the carbon isotope- or nitrogen isotope-replaced 5-aminolevulinic acid for use in the present invention has higher measuring sensitivity than the deuterium-replaced compound.

The isotope-replaced 5-aminolevulinic acid for use in the present invention can be produced by known methods, but it is preferred to produce it by allowing isotope-replaced glycine to react with a microorganism which produces 5-aminolevulinic acid or with an enzyme derived from the microorganism.

Preferred examples of the isotope-replaced glycine as the starting material include those in which the carbon atom of its methylene group is $^{13}$C or the nitrogen atom is $^{15}$N. In the isotope-replaced glycine as the starting material, a single position may be replaced with an isotope or a plurality of positions may be replaced with isotopes. Such isotope-replaced glycine materials can be produced by known methods or obtained as commercial products, such as Glycine-$^{15}$N N15-0019, Glycine-2-$^{13}$C C13-0119 and Glycine-2-$^{13}$C,$^{15}$N M-0019 manufactured by Shoko Tsusho, and Glycine-$^{15}$N 29,929-4, Glycine-2-$^{13}$C 27,943-9 and Glycine-2-$^{13}$C,$^{15}$N 29,932-4 manufactured by Aldrich.

Preferred examples of the 5-aminolevulinic acid-producing microorganism include those using the C$_4$ cycle in the biosynthesis of 5-aminolevulinic acid.

Although there are various microorganisms having such a function, including yeast, fungi, photosynthetic bacteria, and the genus *Rhizobium*, photosynthetic bacteria have high 5-aminolevulinic acid production ability among these microorganisms. Particularly, the genus *Rhodospirillum*, the genus *Rhodopseudomonas*, the genus *Chromatium*, and the genus *Rhodobacter*, more particularly *Rhodobacter sphaeroides*, have higher productivity.

In addition, a mutant having improved productivity of 5-aminolevulinic acid may also be used. Examples of such a mutant include *Rhodobacter sphaeroides* CR-520 (FERM BP-5255; date of international deposition: Oct. 2, 1995), CR-450 (FERM P-14085), CR-386 (FERM P-13159), and CR-286 (FERM P-12542) which have been deposited in National Institute of Bioscience and Human-Technology, Agency of Industrial Science and Technology (Higashi 1-1-3, Tsukuba, Ibaraki, Japan).

In producing the isotope-replaced 5-aminolevulinic acid of interest using a 5-aminolevulinic acid-producing microorganism, the microorganism is cultured in the presence of the above-described isotope-replaced glycine, levulinic acid and the like, and the isotope-replaced 5-aminolevulinic acid of interest is recovered from the resulting culture mixture. The isotope-replaced glycine is added to the medium in an amount of preferably 1 mM to 500 mM, more preferably 5 mM to 240 mM, and levulinic acid is added in an amount of preferably 10 mM to 300 mM, more preferably 20 mM to 180 mM, when the parent strain is used, or preferably 0.1 mM to 100 mM, more preferably 1 mM to 30 mM, when the above-described mutant is used.

Culture conditions of the above-described microorganism are not particularly limited; for example, the above-described CR-450 can be cultured under conditions similar to those for general microorganisms belonging to the genus *Rhodobacter* (JP-A-7-246088). That is, the culture conditions of the CR-450 are not particularly limited, and it may be cultured under aerobic conditions generally at 10 to 40° C., preferably 20 to 35° C., and at a medium pH of preferably 5 to 8, more preferably 5.5 to 7.5. Also, when the medium pH changes during the production of 5-aminolevulinic acid, it is preferred to adjust the pH using an alkali solution of sodium hydroxide, ammonia, potassium hydroxide or the like, or an acid, such as hydrochloric acid, sulfuric acid, phosphoric acid or the like.

In addition, production of the isotope-replaced 5-aminolevulinic acid can be carried out simultaneously with the growth of the microorganism or separately from the cell growth. In this case, the microorganism to be used may be either growth stage cells or resting cells, and such cells can be used as such for the production of the isotope-replaced 5-aminolevulinic acid or after increasing the cell density, for example, by separating the cells by an appropriate means, such as centrifugation or the like, and then suspending the resulting cells in an appropriate solvent, such as a culture medium, a phosphate buffer, or the like.

Since the isotope-replaced 5-aminolevulinic acid is secreted from the cells by culturing, it can be isolated from the resulting culture broth by a certain means, for example, using an ion exchange resin or the like.

Examples of other methods for producing isotope-replaced 5-aminolevulinic acid applicable to the present invention include those which are described in JP-A-3-172191, JP-A-6-169758, JP-A-5-95782, JP-A-6-141875, JP-A-6-153915 and JP-A-8-168391.

On the other hand, production of isotope-replaced 5-aminolevulinic acid using an enzyme produced by a 5-aminolevulinic acid-producing microorganism can be carried out by a known method (JP-A-6-169758), except that isotope-replaced glycine is used as a material.

Isotope-replaced 5-aminolevulinic acid can be produced in the following manner as a typical example.

As the enzyme, a culture broth of a 5-aminolevulinic acid producing-microorganism is used as it is, or cells separated from the culture broth by a certain means, such as centrifugation or the like, are used. Also, the separated cells can be used after washing them with a solution, such as a phosphate buffer or the like, and then suspending them in the solution.

Furthermore, the enzyme in the cells may be used preferably after its purification in the usual way.

That is, the above-described cell suspension is treated with a cell disrupter, such as a sonicator, a French press, a high pressure homogenizer, or the like, the thus disrupted cells are separated to a solid and liquid, for example, by centrifugation or the like, and then purified enzyme is obtained from the resulting enzyme solution by generally used purification means, such as column purification, electrophoresis, or the like.

In addition, the enzyme reaction can be carried out with high efficiency when these resting cells and cell-originated enzyme are immobilized, because the amount of enzyme per unit volume is increased by their immobilization.

The immobilization can be carried out by a usually used method, such as a calcium alginate method, a polyacrylamide gel method, a polyurethane resin method, a photocrosslinkable resin method, or the like.

When the isotope-replaced glycine, succinic acid and the like are allowed to contact with such resting cells or enzymes derived from cells, the reaction starts to produce isotope-replaced 5-aminolevulinic acid.

The reaction conditions is preferably the same as conditions of the mutation and isolation of CR-17 (JP-A-6-169758). Also, light irradiation is not necessary when the enzyme preparation is used.

It is preferred to carry out this reaction by optionally adding an energy source, such as ATP (adenosine triphosphate), pyridoxal phosphate, CoA (coenzyme A), or the like, and an electron donor, such as methanol, ethanol, hydrogen, nicotinamide adenine dinucleotide (NAD), formaldehyde, formic acid, or the like.

Also, a substance inhibiting 5-aminolevulinate dehydratase activity can be added in the reaction.

The isotope-replaced 5-aminolevulinic acid obtained in this manner may be used directly as a crude product or be purified in the usual way depending on each purpose.

The isotope-replaced 5-aminolevulinic acid may be used by converting it into a derivative showing the same function in the body after administration. Examples of such compound include esters, amides or salts of 5-aminolevulinic acid. Among these compounds, examples of the esters and amides include 5-aminolevulinic acid methyl ester, 5-aminolevulinic acid ethyl ester, 5-aminolevulinic acid propyl ester, 5-aminolevulinic acid butyl ester, 5-aminolevulinic acid pentyl ester, 5-aminolevulinic acid hexyl ester, 5-aminolevulinic acid heptyl ester, 5-aminolevulinic acid octyl ester, 5-aminolevulinic acid nonyl ester, 5-aminolevulinic acid dodecyl ester, 5-aminolevulinic acid hexadecyl ester, 5-aminolevulinic acid isopropyl ester, 5-aminolevulinic acid cyclohexyl ester, 5-aminolevulinic acid benzyl ester, 5-aminolevulinic acid phenethyl ester, 5-aminolevulinic acid-3-phenylpropyl ester, 5-aminolevulinic acid ethoxyethyl ester, 5-aminolevulinic acid-2-(hydroxymethyl)tetrafuranyl ester, 5-aminolevulinic acid-2-(hydroxymethyl)-tetrahydropyranyl ester, 5-aminolevulinic acid acetamide, 5-aminolevulinic acid-n-hexanamide, 5-aminolevulinic acid-n-nonanamide, and the like. Examples of the salts include inorganic salts, such as hydrochloride, hydrobromide, hydroiodide, nitrate, phosphate, and the like, organic salts, such as succinate, oxalate, fumarate, maleate, lactate, tartarate, citrate, acetate, glycolate, methanesulfonate, toluenesulfonate, and the like, alkali metal salts, alkaline earth metal salts, ammonium salts, alkylammonium salts, and the like. In addition, these isotope-replaced 5-aminolevulinic acid and esters, amides, and salts thereof may form hydrates or solvates. These compounds and methods for their synthesis are described in JP-A-4-9360.

The agent for diagnosing or treating malignant tumors of the present invention contains the above-described isotope-replaced 5-aminolevulinic acid or a derivative thereof as the active ingredient, and their dosage forms are not particularly limited with the proviso that they do not exert bad influences upon the living body. However, it is necessary to pay attention to pH when used as a solution. That is, since the active ingredient is oxidatively decomposed under alkaline conditions of pH 8 or more, it is not preferred to put the solution under the alkaline conditions for a long time. When preparation of a drug for injection requires alkaline conditions, it is preferred to carry out the treatment within a short time. Also, when a long term preservation is inevitable, it is preferred to reduce dissolved oxygen in the solution by an appropriate means, such as nitrogen purging or the like.

The pH is preferably 8 or less, more preferably 7 or less, and most preferably 6.1 or less. Although not particularly limited, the lower limit of the pH is preferably from 2 to 3.

The administration method of the agent for diagnosing or treating malignant tumors of the present invention is not particularly limited; for example, it may be administered by oral administration, intravenous injection, absorption through its application to an affected part and its peripheral area or by inhalation in the form of aerosols. It can also be administered as suppositories.

When treatment is also an object in addition to diagnoses, the dose may be preferably from 10 mg to 10 g, more preferably from 100 mg to 1 g, per kg body weight in the case of whole body administration, but such a dose can be reduced in the case of topical administration, such as application or the like. When diagnosis is a sole object, the dose can be reduced to a considerably smaller level, although it depends on the purity of the isotope of compound to be used and sensitivity of the measuring machine. When existing instruments are used and the isotope purity is 100%, 1/10 or less of the dose of the case of treatment may be sufficient. It is expected that the dose at the time of diagnosis will be reduced with the improvement of the sensitivity of instruments in the future, but there will be no problem in the case of a large dose. However, administration with a dose larger than the case of treatment is economically disadvantageous. When diagnosis and treatment are simultaneously carried out, economical burden can be reduced by decreasing the isotope purity through the addition of isotope-free 5-aminolevulinic acid.

Regarding the period of time after administration of the drug until the measurement or treatment, the existing ratio of porphyrins becomes maximum during 1 to 8 hours after the administration in many cases, although it slightly varies depending on each tumor of interest. From the time-lapse point of view, accumulation of porphyrins is quick in tumors and slow in normal tissues. When a treatment is carried out, it is most effective to measure the time for maximum existing ratio of porphyrins in each tumor of patient and then carry out photokinetic treatment at the time of the maximum existing ratio.

Regarding the photokinetic treatment, completely the same techniques in the case of the use of 5-aminolevulinic acid which is not replaced with an isotope can be used (C. S. Loh et al., *Br. J. Cancer*, 68: 41–51 (1993)). That is, a method can be used in which cancer cells are selectively killed by irradiating a light to porphyrins induced by administering 5-aminolevulinic acid and accumulated in the cancer cells specifically.

In this case, the light irradiation for use in the treatment may be effective by any light source, but it is preferred that the light source contains the absorption wavelength of porphyrins. Such a wavelength is within the range of preferably 400 nm to 800 nm, more preferably 600 nm to 700 nm. The carcinostatic effect becomes strong as the illumination intensity of the irradiating light increases, but too strong intensity will also damage normal cells, so that it is essential to carry out the irradiation in response to the size and depth of each cancer. In the case of certain cancers, such as lung cancer, gastric cancer, pharyngeal cancer, rectum cancer, large bowel cancer, duodenal cancer, bladder cancer, and the like, PDT treatment can be carried out without surgical operation by irradiating laser beams in combination with an endoscope. When laser beams are used, degree of the irradiation can be controlled by the irradiation time. Pulse irradiation is also effective in this case. Since porphyrins induced by the administration of 5-aminolevulinic acid or a derivative thereof and accumulated in cancer cells specifically act as a sensitizing agent, cancer cells are damaged by the light irradiation more seriously than normal cells, but it is preferred as a matter of course to carry out the operation in such a manner that the light is irradiated to cancer cells as many as possible at the time of the treatment. In view of this point, laser beams are an advantageous light source because the focus is easily narrowed.

The treatment may be carried out once or repeated many times.

It is needless to say that the diagnostic agent of the present invention can be used effectively to know whether the effect of the treatment was sufficient. In other words, the present invention is an invention of a diagnostic agent which is also a therapeutic agent at the same time, that can be used both as a diagnostic agent and as a therapeutic agent.

Influences caused by the isotope replacement can be practically neglected.

The principle of the diagnostic method using the diagnostic agent of the present invention is based on the phenomenon that porphyrins, typified by protoporphyrin IX, as metabolites are accumulated in malignant tumors when 5-aminolevulinic acid is administered. The reason for the occurrence of this phenomenon has been studied at various research organizations but distinct results have not so far been obtained, though there is a hypothesis that the activity of ferrochelatase which metabolizes protoporphyrin IX into its corresponding heme may be low in malignant tumors.

EXAMPLES

The present invention is explained based on Examples below in detail; however, the present invention is not limited thereto.

Production Example 1

Into a 2 L fermentor, 1 L of a medium having a composition shown in Table 2 (medium 1) was put, sterilized at 121° C. for 15 minutes and then cooled down to room temperature.

A mutant of a photosynthetic bacterium, CR-520 (FERM BP-5255), which had been cultured in advance under shaking using a 1 L Sakaguchi flask containing 200 ml of the medium was inoculated into the fermentor, and the fermentation was carried out at 30° C. with an aeration rate of 0.1 v/v/m under stirring at 200 rpm. After 48 hours of the culturing, 3 g of glycine-$^{15}$N (Atom %—99, manufactured by Shoko Tsusho), 5 mM of levulinic acid, 50 mM of glucose and 1% by weight of yeast extract were added to the medium, and the medium pH was adjusted to a value of from 6.5 to 7 with 1 N sodium hydroxide and 1 N sulfuric acid. The aeration rate was reduced to 0.014 v/v/m, and nitrogen gas was supplied at 0.086 v/v/m. The agitation speed was changed to 500 rpm. The culturing was continued until 84 hours under these conditions. The concentration of 5-aminolevulinic acid after the culturing was 2.3 g/L.

The thus obtained culture broth was pre-treated in accordance with the pre-treatment method described in *Biochem. J.*, 219: 883–889 (1984) to produce 2-methyl-3-acetyl-4-(3-propionate pentafluorobenzyl ester)pyrrole, and the ratio of the thus obtained molecular peak of 136 ($M^+$-($C_7H_2F_5$+$CH_2CO_2$)) derived from 5-aminolevulinic acid having $^{14}$N to molecular peak of 137 ($M^+$-($C_7H_2F_5$+$CH_2CO_2$)) derived from 5-aminolevulinic acid having $^{15}$N was compared to calculate the labeling ratio which was 48%.

It can be understood by this example that the isotope contained in glycine was transferred into the thus produced 5-aminolevulinic acid as intended.

TABLE 2

| | g/L (distilled water) |
|---|---|
| Glucose | 9.0 |
| Sodium glutamate | 3.8 |
| Dipotassium hydrogenphosphate | 0.5 |
| Potassium dihydrogenphosphate | 0.5 |
| Ammonium sulfate | 1.3 |
| Magnesium sulfate | 0.2 |
| Magnesium chloride | 0.053 |
| Manganese sulfate | $1.2 \times 10^{-3}$ |
| Nicotinic acid | $1.2 \times 10^{-3}$ |
| Biotin | $1.0 \times 10^{-5}$ |
| Thiamin | $1.0 \times 10^{-3}$ |
| Yeast extract | 2.0 |

Production Example 2

The procedure of Production Example 1 was repeated, except that the amount of glycine-$^{15}$N was changed to 6 g. The concentration of the thus produced 5-aminolevulinic acid was 2.6 g/L and the labeling ratio was 88%.

It can be understood from this example that the higher the concentration of labeled glycine, the higher labeling ratio of produced 5-aminolevulinic acid.

Production Example 3

The procedure of Production Example 2 was repeated, except that 6 g of glycine-2-$^{13}$C (Atom %–99, manufactured by Shoko Tsusho) was used; and the concentration of the thus produced 5-aminolevulinic acid was 2.5 g/L and the labeling ratio calculated from the ratio of a molecular peak of 136 ($M^+$-($C_7H_2F_5$+$CH_2CO_2$)) derived from 5-aminolevulinic acid having $^{12}$C to a molecular peak of 137 ($M^+$-($C_7H_2F_5$+$CH_2CO_2$)) derived from 5-aminolevulinic acid having $^{13}$C was 91%.

Production Example 4

Cultured cells obtained in the same manner as in Production Example 3 were washed three times with a Tris-HCl buffer (pH 8.1) and disrupted using a French press to prepare a crude enzyme solution having a protein concentration of 10 mg/ml. This was mixed with 10 mM ATP, 1 mM CoA-SH, 1 mM pyridoxal phosphate, 2 mM succinyl-coA, 10 mM magnesium chloride, 50 mM Tris-HCl buffer, 0.3 g/L of glutathione, and 1 g/L of glycine-2-$^{13}$C (atom %–99, manufactured by Shoko Tsusho), and the mixture was incubated at 33° C. for 3 hours. After the incubation, the concentration of the thus obtained 5-aminolevulinic acid was measured to be 0.18 g/L. The labeling ratio calculated by the same method as in Production Example 3 was 98%. The results of the NMR spectrum are shown in FIG. 1.

Thus, it can be understood that 5-aminolevulinic acid containing an isotope can also be produced by an enzymatic method. This production example has an advantage of a high labeling ratio, though the productivity is lower than that of the culturing method. In addition, since the enzymatic method is generally resistant to radiation injury in comparison with biological bodies, it will be advantageous for producing 5-aminolevulinic acid containing a radioactive isotope.

Example 1

Preparation of Experimental Animal:

Nude mice (female BALB Cnu/nu, about 8 mm in cancer diameter) were used after 3 weeks of the transplantation of $2 \times 10^6$ cells/animal of human ovarian cancer cisplatin-resistant cultured cell A2480CP to the right-side body subcutaneously.

Preparation of $^{13}$C-labeled 5-aminolevulinic Acid Aqueous Solution:

5-Aminolevulinic acid hydrochloride in which the 5-position carbon was replaced with $^{13}$C (Production Example 4) was used. The 5-aminolevulinic acid hydrochloride in which the 5-position carbon was replaced with $^{13}$C was dissolved in distilled water at a ratio of 25 g/L, and the solution was neutralized to pH 7 with sodium hydroxide. The sodium chloride content of this solution became 0.88% by the neutralization.

Administration Test and Measurement:

The thus neutralized solution was sterilized by immediately passing through a 0.22 µm filter and administered from the mouse caudal vein at a ratio of 12 µl per g body weight. This dose corresponds to 300 mg administration of 5-aminolevulinic acid hydrochloride per 1 kg body weight. After 2, 4 and 8 hours of the administration, mice were sacrificed and subjected to bloodletting, and then the cancer cells and femoral part were excised and packed in 10 mmφ NMR sample tubes to the same volume to measure $^{13}$C-NMR by super-conductive NMR, JNM-A400 manufactured by JEOL, at an observation frequency of 100.50 MHz using a proton decoupling method.

After the measurement, peak areas of from 90 to 160 ppm were integrated, and relative values were calculated based on the value 100 of the first animal after 8 hours of the administration. The test was carried out using two animals for each condition. The results are shown in Table 3.

TABLE 3

| $^{13}$C Area integrated value | Cancer cells | Femoral muscle | Relative ratio (cancer/muscle) |
|---|---|---|---|
| 2 Hours after administration | | | |
| First animal | 19 | 11 | 1.7 |
| Second animal | 22 | 13 | 1.7 |
| 4 Hours after administration | | | |
| First animal | 89 | 18 | 4.9 |
| Second animal | 73 | 11 | 6.6 |
| 8 Hours after adininistration | | | |
| First animal | 100 | 51 | 2.0 |
| Second animal | 87 | 62 | 1.4 |

It is apparent from Table 3 that the existing frequency of $^{13}$C is higher in the cancer cells than in the muscle. It was indicated based on these results that malignant tumors can be diagnosed by administering $^{13}$C-labeled 5-aminolevulinic acid and examining the region where $^{13}$C is accumulated through the measurement of $^{13}$C-NMR. Although a model experiment was carried out using an animal in this example, it can be expected easily from the results of this example that this method can be applied to the diagnostic imaging of malignant tumors in human by combining it with medical MRI techniques.

INDUSTRIAL APPLICABILITY

Diagnosis of malignant tumors can be carried out effectively using the diagnostic agent of the present invention. In particular, it can correspond to malignant tumors existing in deep regions of tissues, which cannot be diagnosed easily by the prior art techniques. Also, it can be applied to an epoch-making method for the diagnosis of malignant tumors, as a non-destructive technique by which diagnostic imaging can also be carried out. In addition, photokinetically treatments can be carried out using the isotope-replaced 5-aminolevulinic acid of the present invention.

We claim:

1. A method for detecting and treating a malignant tumor, which method comprises;
   administering a tumor detecting effective amount, to a host in need of detection of a malignant tumor, of 5-aminolevulinic acid or a derivative thereof in which at least one carbon atom of said 5-aminolevulinic acid is a carbon isotope and/or a nitrogen atom in its amino group is a nitrogen isotope, and where said derivative is an ester, amide, salt, hydrate or solvate of said 5-aminolevulinic acid;
   detecting the malignant tumor using NMR; and
   administering an effective amount of said 5-aminolevulinic acid or derivative thereof, in which at least one carbon atom of said 5-aminolevulinic acid is a carbon isotope and/or a nitrogen atom in its amino group is a nitrogen isotope, and where said derivative is an ester, amide, salt, hydrate or solvate of said 5-aminolevulinic acid, to kill said malignant tumor.

2. The method of claim 1 wherein said 5-aminolevulinic acid or derivative thereof is used in combination with a diagnostically acceptable carrier.

3. A method for detecting and treating a malignant tumor, which method comprises;
   administering a tumor detecting effective amount, to a host in need of detection of a malignant tumor, of a 5-aminolevulinic acid or a derivative thereof in which at least one carbon atom of said 5-aminolevulinic acid is a carbon isotope and/or a nitrogen atom in its amino group is a nitrogen isotope, and where said derivative is an ester, amide, salt, hydrate or solvate of said 5-aminolevulinic acid to thereby accumulate the carbon isotope and/or the nitrogen isotope in the malignant tumor;
   detecting the carbon and/or the nitrogen isotope using NMR to thereby identity the position of the malignant tumor; and
   administering an effective amount of said 5-aminolevulinic acid or a derivative thereof,
   in which at least one carbon atom of said 5-aminolevulinic acid is a carbon isotope and/or a nitrogen atom in its amino group is a nitrogen isotope, and where said derivative is an ester, amide, salt, hydrate or solvate of said 5-aminolevulinic acid, to kill said malignant tumor.

4. The method of claim 3, wherein the malignant tumor is detected and treated in a living host.

5. The method of claim 1, wherein the killing of said malignant tumor is by a photokinetic method.

6. The method of claim 3, wherein the killing of said malignant tumor is by a photokinetic method.

7. The method of claim 1, wherein the carbon isotope is used and it is the $^{13}$C or $^{14}$C isotope.

8. The method of claim 7, wherein the carbon isotope is used and it is the $^{13}$C isotope and the NMR is $^{13}$C-NMR.

9. The method of claim 3, wherein the carbon isotope is used and it is the $^{13}$C or $^{14}$C isotope.

10. The method of claim 9, wherein the carbon isotope is used and it is the $^{13}$C isotope and the NMR is $^{13}$C-NMR.

11. The method of claim 1, wherein the nitrogen isotope is used and it is the $^{15}$N isotope.

12. The method of claim 3, wherein the nitrogen isotope is used and it is the $^{15}$N isotope.

13. The method of claim 1, wherein said derivative is used and said derivative is the ester.

14. The method of claim 3, wherein said derivative is used and said derivative is the ester.

15. The method of claim 1, wherein said derivative is used and said derivative is the amide.

16. The method of claim 3, wherein said derivative is used and said derivative is the amide.

17. The method of claim 1, wherein said derivative is used and said derivative is the salt.

18. The method of claim 3, wherein said derivative is used and said derivative is the salt.

19. The method of claim 1, wherein said derivative is used and said derivative is the hydrate.

20. The method of claim 3, wherein said derivative is used and said derivative is the hydrate.

21. The method of claim 1, wherein said derivative is used and said derivative is the solvate.

22. The method of claim 3, wherein said derivative is used and said derivative is the solvate.

23. The method of claim 1, wherein the detecting and treating are conducted using a total dose of from 10 mg to 10 g per kg body weight.

24. The method of claim 3, wherein the detecting and treating are conducted using a total dose of from 10 mg to 10 g per kg body weight.

25. The method of claim 1, wherein the detecting and treating are performed with the same 5-aminolevulinic acid or a derivative thereof in which at least one carbon atom of said 5-aminolevulinic acid is a carbon isotope and/or a nitrogen atom in its amino group is a nitrogen isotope, and wherein said derivative is an ester, amide, salt, hydrate or solvate of said 5-aminolevulinic acid.

26. The method of claim 3, wherein the detecting and treating are performed with the same 5-aminolevulinic acid or a derivative thereof in which at least one carbon atom of said 5-aminolevulinic acid is a carbon isotope and/or a nitrogen atom in its amino group is a nitrogen isotope, and wherein said derivative is an ester, amide, salt, hydrate or solvate of said 5-aminolevulinic acid.

27. The method of claim 1, wherein said malignant tumor exists in a deep region of tissue.

28. The method of claim 3, wherein said malignant tumor exists in a deep region of tissue.

29. The method of claim 1, wherein the malignant tumor is detected and treated in a living host.

* * * * *